United States Patent [19]

Bannister et al.

[11] 4,022,889

[45] May 10, 1977

[54] THERAPEUTIC COMPOSITIONS OF ANTIBIOTIC U-44,590 AND METHODS FOR USING THE SAME

[75] Inventors: Brian Bannister; Clarence DeBoer, both of Kalamazoo; Harold E. Renis, Portage, all of Mich.

[73] Assignee: The Upjohn Company, Kalamazoo, Mich.

[22] Filed: June 12, 1975

[21] Appl. No.: 586,232

Related U.S. Application Data

[63] Continuation of Ser. No. 471,309, May 20, 1974, abandoned.

[52] U.S. Cl. .............................................. 424/181
[51] Int. Cl.$^2$ ........................................ A61K 31/71
[58] Field of Search ................................... 424/181

[56] References Cited

UNITED STATES PATENTS 3,907,779   9/1975   DeBoer et al. ............. 260/211.5 R

*Primary Examiner*—Sam Rosen
*Attorney, Agent, or Firm*—William G. Jameson; Sidney B. Williams, Jr.; Roman Saliwanchik

[57] ABSTRACT

Pharmaceutical compositions of antibiotic U-44,590 and derivatives thereof which can be used to treat Gram-negative and Gram-positive bacterial and viral diseases in humans and animals.

32 Claims, No Drawings

THERAPEUTIC COMPOSITIONS OF ANTIBIOTIC U-44,590 AND METHODS FOR USING THE SAME

BRIEF SUMMARY OF THE INVENTION

This is a continuation of application Ser. No. 471,309 filed May 20, 1974, now abandoned.

Disclosed are pharmaceutical compositions of antibiotic U-44,590 and derivatives thereof which can be used to treat Gram-negative and Gram-positive bacterial and viral diseases in humans and animals.

Antibiotic U-44,590 is a novel antibiotic producible by culturing the novel actinomycete Streptomyces platensis var. clarensis, NRRL 8035, in an aqueous nutrient medium under aerobic conditions. Various derivatives of U-44,590 can be prepared as disclosed, infra. U-44,590 and its derivatives have the property of adversely affecting the growth of Gram-negative and Gram-positive bacteria, for example, Streptococcus hemolyticus, Klebsiella pneumoni Salmonella Sp., Serratia marcescens, Pasteurella multocida, Hemophilis Sp., Proteus morgani and Proteus rettgeri. Accordingly, U-44,590 and its derivatives can be used alone or in combination with other antibiotic agents to prevent the growth of or reduce the number of bacteria, as disclosed above, in various environments.

U-44,590 and its derivatives are also active against DNA viruses, for example, the Herpes virus and, thus, can be used to control such virus where is presence is not desired.

DETAILED DESCRIPTION OF THE INVENTION

Chemical and Physical Properties of U-44,590

Elemental Analysis: Calcd. for $C_9H_{15}N_3O_5$: C, 44.08; H. 6.17; N, 17.13. Found: C, 44.14; H, 6.08; N, 17.36.

Molecular Weight: 245 (Determined by mass spectrometry)

Melting Point Range: 141°– 142° C.

Specific Rotation: $[\alpha]_D^{25} = -5°$ (c, 0.9030 in $H_2O$)

Solubilities: Highly soluble in water, and lower alcohols, for example, methanol and ethanol; relatively insoluble in $Me_2CO$, EtOAc, hydrocarbons, $CH_2Cl_2$ and $CHCl_3$.

Infrared Absorption Spectra; U-44,590 has a characteristic infrared absorption spectrum when suspended in a mineral oil mull. Peaks are observed at the following wave lengths expressed in reciprocal centimeters:

| Band Frequency (Wave Numbers) | Intensity |
| --- | --- |
| 3440 | M |
| 3400 | M |
| 3340 | M |
| 3190 | M |
| 3080 | M |
| 3000 | W |
| 2960 (N = Nujol) | S |
| 2930 (N) | S |
| 2860 (N) | S |
| 1695 sh. | S |
| 1683 | S |
| 1510 | M |
| 1503 | M |
| 1483 | M |
| 1463 (N) | S |
| 1440 | S |
| 1421 | M |
| 1407 | M |
| 1396 | M |
| 1375 (N) | W |
| 1350 | M |
| 1315 | W |
| 1300 | W |
| 1280 | W |
| 1276 | W |
| 1262 | W |
| 1243 | S |
| 1230 sh. | M |
| 1195 | W |
| 1165 | W |
| 1133 | W |
| 1093 | M |
| 1085 | W |
| 1060 | S |
| 1011 | S |
| 985 | M |
| 971 | W |
| 943 | M |
| 885 | W |
| 872 | W |
| 849 | W |
| 826 | W |
| 792 | M |
| 755 | M |
| 735 | W |

Note: sh means a shoulder band.

U-44,590 also has a characteristic infrared absorption spectrum when pressed in a KBr disc. Peaks are observed at the following wave lengths expressed in reciprocal centimeters:

| Band Frequency (Wave Numbers) | Intensity |
| --- | --- |
| 3440 | S |
| 3200 | M |
| 3080 | M |
| 3000 | W |
| 2970 | W |
| 2960 | W |
| 2935 | W |
| 2920 | W |
| 2870 | W |
| 1697 sh. | S |
| 1685 | S |
| 1510 | M |
| 1482 | M |
| 1461 | S |
| 1437 | M |
| 1420 | M |
| 1406 | M |
| 1396 | M |
| 1349 | W |
| 1310 | W |
| 1298 | W |
| 1290 | W |
| 1275 sh. | M |
| 1263 | M |
| 1243 | S |
| 1195 | W |
| 1165 | W |
| 1133 | W |
| 1097 | M |
| 1085 | M |
| 1060 | M |
| 1010 | M |
| 985 | W |
| 971 | W |
| 942 | M |
| 883 | W |
| 870 | W |
| 847 | W |
| 827 | W |
| 791 | M |
| 754 | W |
| 733 | W |

Note: sh means a shoulder band.

Infrared bands intensities, throughout this disclosure, are indicated as "S", "M", and "W" respectively and are approximated in terms of the backgrounds in the vicinity of the bands. An "S" band is of the same order of intensity as the strongest in the spectrum; "M" bands are between 1/3 and 2/3 as intense as the strongest band; and, "W" bands are less than 1/3 as intense as the strongest band. These estimates are made on the basis of a percent transmission scale.

The following is considered to be the structure of U-44,590:

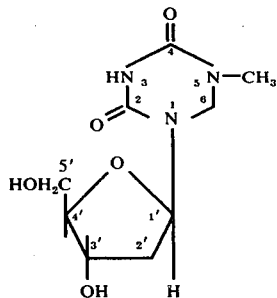

Thus, U-44,590 can be referred to by the trivial name 5,6-dihydro-5-azathymidine, or by its chemical name 1(2-deoxy-α-D-erythro-pentofuranosyl)-5,6-dihydro-5-methyl-s-triazine-2,4-(1H,3H)-dione.

| Antibacterial Activity of U-44,590 | | |
|---|---|---|
| Organism | No. of Strains | Inhibition μg/ml |
| Staphylococcus aureus | 1 | >1000 |
| Streptococcus hemolyticus | 1 | 15.2 |
| Diplococcus pneumoniae | 1 | 500. |
| Klebsiella pneumoniae | 5 | 2.0 – >1000 |
| Salmonella sp. | 4 | 15.6 – >1000 |
| Serratia marcescens | 2 | 125 |
| Pseudomonas aeruginosa | 5 | >1000 |
| Pasteurella multocida | 1 | 125 |
| Hemophilus sp. | 5 | 31.2 – >1000 |
| Proteus vulgaris | 3 | >1000 |
| Proteus mirabilis | 3 | >1000 |
| Proteus morgani | 3 | 62.5 – 250 |
| Proteus rettgeri | 3 | 31.2 – >1000 |

The above antibacterial spectrum was obtained by a standard agar dilution test with the following media and conditions:

Difco Brain Heart Infusion Medium was used for all test bacteria except P. multocida and Hemophilus species which were grown in Difco Blood Agar Base with 5% defibrinated rabbit blood. All were grown aerobically at 37° C. (except Hemophilus species, grown anerobically) 16–18 hours. Inocula were grown overnite (16–18 hours) at 37° C. and used to seed agar at the rate of 0.025 ml. of $10^{-3}$ dilution (approximately 2500 to 25,000 bacteria per drop of inoculum).

In vivo testing of U-44,590 in mice infected with selected microorganisms is as follows:

| | | Activity ($CD_{50}$ in mg/kg) | |
|---|---|---|---|
| Organism | Mice, IP Challenge $LD_{50}$ | Subcutaneous Route | Oral Route |
| Salmonella flexneri | 40 | 38 (25–57) | 62.5 |
| Escherichia coli | 79 | 141 (116–172) | 218 (154–307) |
| Proteus mirabilis | 1259 | 152 (96–240) | 101 (66–156) |
| Proteus vulgaris | 79 150 | 100 (66–152) | <62.5 ~30 |
| Streptococcus hemolyticus | 100 | — | >160 |

ANTIVIRAL ACTIVITY OF U-44,590

The following is an example of the antiviral activity of antibiotic U-44,590. The antibiotic is administered subcutaneously to mice which are inoculated intravenously with Herpes simplex virus. Treatment is initiated 2 hours prior to viral infection and is followed by treatment four times daily for five consecutive days. A detailed account of the materials and methods and results are as follows:

Male mice, weighing approximately 20 gm. each, are divided into 4 groups of 20. Group 1 is treated with saline, Group 2 with 400 mg./kg./dose (mkd) U-44,590, Group 3 with 200 mkd U-44,590, and Group 4 with 100 mkd U-44,590. The antibiotic is dissolved in saline and administered subcutaneously in the nape of the neck at 8 a.m., 12 noon, 4 p.m., and 8 p.m. on days 0, 1, 2, 3, and 4. Herpes virus at $10^{-1.5}$ dilution, 0.05 ml/mouse, equivalent to a viral dose of 40 $LD_{50}$s, is inoculated into the tail vein at 10 a.m. on day 0. Paralysis and death are recorded daily.

Hind leg paralysis usually preceded death by 1–2 days. All mice died that became paralyzed. Death pattern of the 4 groups, as shown in the curves which follow, illustrates the dose response obtained. Statistical analysis of the results at day 11 indicates that all 3 treated groups are significantly different from the control group (1).

Antibiotic U-44,590 vs. Herpes virus in Mice (20 mice per group)

●—● Saline
○—○ U-44,590 at 100 mg./kg./dose
△—△ U-44,590 at 200 mg./kg./dose
□—□ U-44,590 at 400 mg./kg./dose -continued Antibiotic U-44,590 vs. Herpes virus in Mice (20 mice per group)

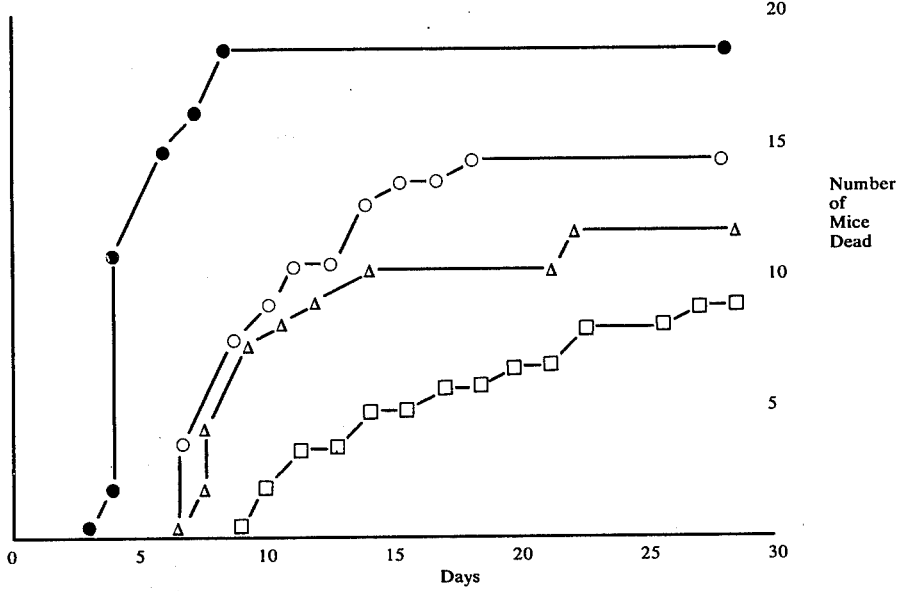

THE MICROORGANISM

The microorganism used for the production of U-44,590 is Streptomyces platensis var. clarensis, NRRL 8035. A subculture of this microorganism can be obtained from the permanent collection of the Northern Regional Research Laboratory, U.S. Department of Agriculture, Peoria, Illinois, U.S.A.

The microorganism of this invention was studied and characterized by Alma Dietz of the Upjohn Research Laboratories.

A new soil isolate with hygroscopic spore masses, but with smooth, hat-shaped (crescent) or brazil-nut -shaped (elliptical) spores, has been found to differ in certain characteristics from the type culture Streptomyces platensis. An outstanding difference of the new culture is the production of antibiotic U-44,590. The new isolate can be recognized as a variant of Streptomyces platensis by its cultural, microscopic, and biochemical characteristics. Therefore, it is proposed that this new isolate be designated Streptomyces platensis var. clarensis Dietz var. nova. Rule 7 of the International Code of Nomenclature of Bacteria [International Code of Nomenclature of Bacteria. 1966. Edited by the Editorial Board of the Judicial Commission of the International Committee on Nomenclature of Bacteria. Int. J. Syst. Bacteriol. 16: 459–490] was applied in designating the variety epithet.

Streptomyces platensis var. clarensis is compared with the type species Streptomyces platensis Pittenger and Gottlieb [Shirling, E. B., and D. Gottlieb. 1968. Cooperative description of type cultures of Streptomyces III. Additional species descriptions from first and second studies. Int. J. Syst. Bacteriol. 18:279-392] [Tresner, H. D., E. J. Backus, and Jean A. Hayes. 1967. Morphological spore types in the Streptomyces hygroscopicus-like complex. Appl. Microbiol. 15:637-639] NRRL 2369, and two recently characterized strains: Streptomyces platensis NRRL 3593 [Evans, Ralph Henry Jr., and Samuel Owen Thomas. 1971. Antibiotics AH272$\alpha_2$ and AH272$\beta_2$ and process for producing same. U.S. Pat. 3,592,925] and Streptomyces platensis NRRL 3761 [Okuda, Tomohau, and Shigemi Awatagouchi. 1973. Antibiotics YL 704 and preparation thereof. U.S. Pat. No. 3,718,742].

Color characteristics:

Aerial growth white to yellow to gray. Moist black hygroscopic patches on some media. Melanin-negative. Appearance on Ektachrome [Dietz. A. 1954. Ektachrome transparencies as aids in actinomycete classification. Ann. N.Y. Acad. Sci. 60:152-154] is given in Table 1. Reference color characteristics are given in Tables 2 and 3. The new culture may be placed in the White (W), Yellow (Y), and Gray (GY) color series of Tresner and Backus [Tresner, H. D., and E. J. Backus. 1963. System of color wheels for streptomycete taxonomy. Appl. Microbiol. 11:335-338].

Microscopic characteristics:

Spore chains in tight spirals uncoiling to long open spirals. Spore chains spiral (S) in the sense of Pridham et al. [Pridham, T. G., C. W. Hesseltine, and R. G. Benedict. 1958. A guide for the classification of streptomycetes according to selected groups. Placement of strains in morphological sections. Appl. Microbiol. 6:52-79]. Spore hat-shaped (crescent) or Brazil-nut (elliptical) shaped. Spores are the platensis-type of Tresner and Backus [Tresner, H. D., E. J. Backus, and Jean A. Hayes. 1967. Morphological spore types in the Streptomyces hygroscopicus-like complex. Appl. Microbiol. 15:637-639]. Spore silhouette smooth by direct observation with the electron microscope. Spore surface ridged with surface markings by the carbon replication technique of Dietz and Mathews [Dietz, A. and J. Mathews. 1962. Taxonomy by carbon replication. I. An examination of Streptomyces hygroscopicus. Appl. Microbiol. 10:258-263].

Cultural and biochemical characteristics: See Table 4, infra. Carbon utilization:

Growth on carbon compounds was determined in the synthetic medium of Pridham and Gottlieb [Pridham, T. G., and D. Gottlieb. 1948. The utilization of carbon compounds by some Actinomycetales as an aid for species determination. J. Bacteriol. 56:107-114], Table 5 and in the synthetic medium of Shirling and Gottlieb [Shirling, E. B. and D. Gottlieb. 1966. Methods for characterization of Streptomyces species. Int. J. Syst. Bacteriol. 16:313-340], Table 6.

Temperature:

The cultures grew well at 18°–37° C. on Bennett's, Czapek's sucrose, maltose-tryptone, and Hickey-Tresner agars. Optimum growth was at 24°–37° C. The new culture and the type culture did not grow at 45°–55° C. The cultures designated NRRL 3593 and NRRL 3761 grew at 45° C. but not at 55° C.

Antibiotic-producing properties: See Table 7, infra.

Source: Soil

Type culture:

Streptomyces platenis Pittenger and Gottlieb NRRL 2364.

Type variety:

Streptomyces platensis var. platensis NRRL 2364.

Variety:

Streptomyces platensis var. clarensis Dietz var. nova.

Table 1

| Agar medium | Determination | S. platensis var. clarensis NRRL 8035 | S. platensis NRRL 2364 | S. platensis NRRL 3593 |
|---|---|---|---|---|
| Bennett's | S | Lavender-gray with black patches | Lavender-gray | lavender-gray |
|  | R | Cream-yellow-pink | Pink-tan | Yellow |
| Czapek's sucrose | S | Lavender-gray-white | Lavender-gray | Lavender-gray-white |
|  | R | Cream-yellow | Pale pink-gray | Bright yellow |
| Maltose-tryptone | S | Lavender-gray with black patches | Lavender-gray | Lavender-gray |
|  | R | Cream-yellow-pink | Pink-tan | Yellow-tan |
| Peptone-iron | S | Trace gray-white | Trace lavender-gray | Trace gray |
|  | R | Cream yellow | Yellow | Yellow-tan |
| 0.1% Tyrosine | S | Trace gray with black patches | Pale Lavender-gray | Trace gray |
|  | R | Pale yellow | Pink-tan | Colorless |
| Casein starch | S | Lavender-gray | Lavender-gray | Lavender-gray |
|  | R | Pale cream | Pale gray-yellow | Cream |

S = Surface
R = Reverse
*Dietz, A. 1954. Ektachrome transparencies as aids in actinomycete classification. Ann. N.Y. Acad. Sci. 60:152–154

Table 2

Reference Color Characteristics of Streptomyces platensis Cultures

| Agar Medium | Determination | Color Harmony Manual 3rd ed. 1948* | | | |
|---|---|---|---|---|---|
| | | S. platensis v. clarensis NRRL 8035 | S. platensis NRRL 2364 | S. platensis NRRL 3593 | S. platensis NRRL 3761 |
| Bennett's | S | 2lh(g) to d(g) | 2fe(m) | 2dc(m) | 2dc(m) |
|  | R | 2fb(g) | 3gc(g) | 1 ½gc(g) | 2ec(g) |
|  | P | — | — | — | — |
| Czapek's sucrose | S | a(g) to 2ba(g) | 3ge(m) | 2ba(m) | b(m) |
|  | R | 2fb(g) | 3ge(g) | 1 ½ic(g) | 2ca(g) |
|  | P | — | — | — | — |
| Maltose-tryptone | S | 3fe(g) | 2ge(m) to b(m) | 2dc(m) | 2dc(m) |
|  | R | 1 ½fb(g) | 2gc(m) | 1 ½gc(g) | 2gc(m) |
|  | P | — | — | — | — |
| Hickey-Tresner | S | 3ll(m) to 3fe(m) | 3ig(m) | 2dc(m) | 3ge(m) |
|  | R | lec(g) to 2ie(g) | 2ec(m) | 1 ½gc(g) | 2ec(m) |
|  | P | — | — | — | — |
| Yeast extract-malt extract (ISP-2) | S | 3ig(m) | 3ge(m) | 2dc(m) to 2ba(m) | 3ge(m) |
|  | R | lec(g) | 3ie(g) | 1 ½lc(g) | 2gc(m) |
|  | P | — | — | 1 ½lg(m) | — |
| Oatmeal (ISP-3) | S | 3ig(m) | 3ig(m) | 3ge(m) | 3li(m) |
|  | R | lec(g) | 3ie(g) | 2gc(g) | 2ca(g) |
|  | P | — | — | — | — |
| Inorganic salts-starch (ISP-4) | S | 3li(m) to 3ge(m) | 3li(m) | 2dc(m) | 2ge(m) |
|  | R | 2fb(g) | 2ca(m) to 3ie(m) | 2ec(g) | 2ec(g) |
|  | P | 2gc(g) | 3ie-trace | — | — |
| Glycerol-asparagine (ISP-5) | S | b(m) | 3ge(m) | 2ba(g) | 2ba(m) |
|  | R | 2ec(g) | 2gc(m) | 2fb(m) | 3ca(g) |
|  | P | — | — | — | — |

*Jacobson, E., W.C. Granville, and C.E. Foss. 1948. Color harmony manual, 3rd ed.Container Corporation of America, Chicago, Illinois Reference Color Characteristics of Streptomyces platensis Cultures

| Agar Medium | Determination | NBS Circular 553, 1955** | | | |
|---|---|---|---|---|---|
| | | S. platensis v. clarensis NRRL 8035 | S. platensis NRRL 2364 | S. platensis NRRL 3593 | S. platensis NRRL 3761 |
| Bennett's | S | 112m,113g | 94g,112gm | 93gm | 93gm |

Table 2-continued

|  |  |  |  |  |  |
|---|---|---|---|---|---|
|  | R | 87g,89m | 76gm | 102g,105gm | 90gm |
|  | P | — | — | — | — |
| Czapek's | S | 263gm,92gm | 79m,94m | 92gm | 263gm,92gm |
| sucrose | R | 87g,89m | 79m,94m | 87gm | 89gm |
|  | P | — | — | — | — |
| Maltose-tryptone | S | 63gm | 94m,109gm, 263m,264g | 93gm | 93gm |
|  | R | 87g | 90gm | 102g,105gm | 90gm |
|  | P | — | — | — | — |
| Hickey-Tresner | S | 80m,95g | 80m,95g | 93gm | 79m,94m |
|  | R | 121m,122g,91gm 94g,106g | 90gm | 102g,105gm | 90gm |
|  | P | — | — | — | — |
| Yeast extract-malt extract (ISP-2) | S | 80m,95g | 79m,94m | 93gm,92gm | 79m,94m |
|  | R | 121m,122g | 76m,77g | 87m | 90gm |
|  | P | — | — | — | — |
| Oatmeal (ISP-3) | S | 80m,95g | 80m,95g | 79m,94m | 80m,95g |
|  | R | 121m,122g | 76m,77g | 90gm | 89gm |
|  | P | — | — | — | — |
| Inorganic salts-starch (ISP-4) | S | 80m,95g | 80m,95g | 93gm | 94m,109g |
|  | R | 87g,89m | 89gm,76m,77g | 90gm | 90gm |
|  | P | 90gm | 76m,77g | — | — |
| Glycerol-asparagine (ISP-5) | S | 263m,264g | 79m,94m | 92gm | 92gm |
|  | R | 90gm | 90gm | 87g,89m | 73gm |
|  | P | — | — | — | — |

**Kelly, K. L., and D. B. Judd. 1955. The ISCC-NBS method of designating colors and a dictionary of color names. U.S Dept. Comm. Circ. 553
S = Surface
R = Reverse
P = Pigment
(g) = glossy chip surface
(m) = matte chip surface

Table 3

Color Code for Table 2

| Color Harmony Manual 3rd ed. 1948* | | NBS Circular 553, 1955** | |
|---|---|---|---|
| Color Chip | Color Name | Color Chip | Color Name |
| a | White | 263 gm | White |
| b | Oyster white | 263 m | White |
|  |  | 264 g | Light gray |
| lec | Light citron gray, putty | 121 m | Pale yellow-green |
|  |  | 122 g | Grayish yellow-green |
| 1 ½fb | Pastel yellow | 87 g | Moderate yellow |
| 1 ½gc | Dusty yellow | 102 g | Moderate greenish yellow |
|  |  | 105 gm | Grayish greenish yellow |
| 1 ½ic | Light antique gold | 87 gm | Moderate yellow |
| 1 ½lc | Gold |  |  |
| 1 ½lg | Golden olive | 107 g | Moderate olive |
| 2ba | Pearl, shell tint | 92 gm | Yellowish white |
| 2ca | Light ivory, eggshell | 89 gm | Light yellow |
| 2dc | Natural, string | 93 gm | Yellowish gray |
| 2ec | Biscuit, ecru, oatmeal, sand | 90 gm | Grayish yellow |
| 2fb | Bamboo, buff, straw, wheat | 87 g | Moderate yellow |
|  |  | 89 m | Pale yellow |
| 2fe | Silver gray | 94 g | Light olive brown |
|  |  | 112 gm | Light olive gray |
| 2gc | Bamboo, chamois | 90 gm | Grayish yellow |
| 2ge | Covert tan, griege | 90 gm | Grayish yellow |
| 2ie | Light mustard tan | 91 gm | Dark grayish yellow |
|  |  | 94 g | Light olive brown |
|  |  | 106 g | Light olive |
| 2ih | Dark covert gray | 112 m | Light olive gray |
|  |  | 113 g | Olive gray |
| 3ca | Pearl pink, shell | 73 gm | Pale orange yellow |
| 3fe | Silver gray | 63 gm | Light brownish gray |
| 3gc | Light tan | 76 gm | Light yellowish brown |
| 3ge | Beige, camel | 79 m | Light grayish yellowish brown |
|  |  | 94 m | Light olive brown |
| 3ie | Camel, maple sugar, tan | 76 m | Light yellowish brown |
|  |  | 77 g | Moderate yellowish brown |
| 3ig | Beige brown, mist brown | 80 m | Grayish yellowish brown |
|  |  | 95 g | Moderate olive brown |
| 3li | Beaver | 80 m | Grayish yellowish brown |
|  |  | 95 g | Moderate olive brown |

* Jacobson, E., W.C. Granville, and C.E. Foss. 1948. Color harmony manual, 3rd ed. Container Corporation of America, Chicago, Illinois
**Kelly, K.L., and D.B. Judd. 1955. The ISCC-NBS method of designating colors and a dictionary of color names. U.S. Dept. Comm. Circ. 553

Table 4

Cultural and Biochemical Characteristics of *Streptomyces platensis* Cultures

| Medium | Determination | *S. platensis v. clarensis* NRRL 8035 | *S. platensis* NRRL 2364 | *S. platensis* NRRL 3593 | *S. platensis* NRRL 3761 |
|---|---|---|---|---|---|
| Agar | | | | | |
| Peptone-iron | S | Pale gray | — | Pale gray | Pale gray-pink |
| | R | Pale olive-tan | Tan | Yellow-tan | Yellow |
| | P | — | — | Yellow | — |
| | O | Melanin-negative | Melanin-negative | Melanin-negative | Melanin-negative |
| Calcium malate | S | Pale gray | Pale tan | Pale gray | Pale gray-white |
| | R | Gray | Pale tan | Gray | Gray |
| | P | — | — | — | — |
| | O | Malate not solubilized | Malate not solubilized | Malate not solubilized | Malate slightly solubilized |
| Glucose asparagin | S | Trace pale gray | Pale pink-tan | Pale gray-pink | Gray-white |
| | R | Pale olive-tan | Pink-tan | Pale yellow-tan | Pale salmon |
| | P | Pale yellow | — | — | — |
| Skim milk | S | Pale gray-pink | Pale pink on edge | Pale gray on edge | Trace white on edge |
| | R | Orange-tan | Pale orange | Pale orange | Yellow |
| | P | Orange-tan | Pale orange | Yellow-orange | Yellow |
| | O | Casein not solubilized | Casein not solubilized | Casein not solubilized | Casein not solubilized |
| Tyrosine | S | Pale gray-pink | white | Pale gray-cream | Pale gray-pink |
| | R | Yellow | Yellow | Yellow | Orange-tan |
| | P | Yellow | Yellow | Yellow | Orange-tan |
| | O | Tyrosine solubilized | Tyrosine solubilized | Tyrosine solubilized | Tyrosine solubilized |
| Xanthine | S | Pale gray-pink | White | Pale gray | Pale gray-pink |
| | R | Yellow | Pale yellow | Pale yellow | Yellow |
| | P | — | — | Pale yellow | — |
| | O | Xanthine slightly solubilized under growth | Xanthine sligthtly solubilized under growth | Xanthine not solubilized | Xanthine solubilized under growth |
| Nutrient starch | S | Pale gray-pink | Pale pink | Pale gray-pink | Pale gray-pink |
| | R | Yellow | Yellow | Lemon-yellow | Pale yellow |
| | P | — | — | Yellow | — |
| | O | Starch hydrolyzed | Starch hydrolyzed | Starch hydrolyzed | Starch hydrolyzed |
| Yeast extract-malt extract | S | Gray with black patches | Pale pink-tan | White | Pale gray-pink |
| | R | Yellow-tan | Red-tan | Deep yellow | Yellow |
| | P | Yellow | Yellow | Yellow | — |
| Bennett's | S | Lavender-gray with black patches | Lavender-gray with black patches | Pale lavender-gray | Heavy gray |
| | R | Olive-gray | Red-tan | Light olive | Cream-tan |
| | P | Pale yellow-olive | Pink-tan | Light olive | — |
| Czapek's sucrose | S | Gray-white | Gray-black in center, light | White | Sparse gray-white |
| | R | Yellow | Gray-green | Yellow | Cream |
| | P | Pale yellow | — | Yellow | — |
| Maltose-tryptone | S | Lavender-gray | Pale gray | Gray-white | Gray-white |
| | R | Olive-green | Cream-yellow- | Olive | Pale olive-cream |
| | P | Olive-yellow | Pale yellow | Pale olive | Pale tan |
| Agar | | | | | |
| Hickey-Tresner (modified) | S | Gray with black center | Black with gray edge | Deep gray-white | Gray with black patches |
| | R | Olive | Olive-tan | Light olive | Pale olive-cream |
| | P | — | Pale olive | Light olive | — |
| Peptone-yeast extract-iron (ISP-6) | S | Pale gray | — | Trace white | — |
| | R | Yellow | Pale yellow | Yellow | Yellow |
| | O | Melanin-negative | Melanin-negative | Melanin-negative | Melanin-negative |
| Tyrosine (ISP-7) | S | Gray with black patches | Gray with black patches | Pale gray-white | Pale salmon |
| | R | Pale olive | Pale cream-pink | Pale olive | Pale red-tan |
| | O | Melanin-negative | Melanin-negative | Melanin-negative | Melanin-negative |
| Gelatin | | | | | |
| Plain | S | White | Colorless vegetative growth | Colorless vegetative growth | Colorless vegetative growth |
| | P | Yellow | Trace tan | Trace brown | — |
| | O | Trace liquefaction | No liquifaction | No liquefaction | No liquefaction |
| Nutrient | S | Trace vegetative growth | Colorless vegetative growt | White | White |
| | P | — | — | Trace yellow | — |
| | O | Trace liquefaction | Trace to no liquefaction | No liquefaction | No liquefaction |
| Broth | | | | | |
| Synthetic nitrate | O | Trace bottom growth Nitrate not reduced to nitrite | Colorless surface pellicle and bottom growth Nitrate not reduced to nitrite | Trace bottom growth Nitrate not reduced to nitrite | Trace bottom growth Nitrate reduced to nitrite |
| Nutrient nitrate | O | Trace white surface ring Flocculent bottom growth Nitrate not reduced to nitrite | Trace white surface ring Flocculent bottom growth Nitrate not reduced to nitrite | Trace bottom growth Nitrate not reduced to nitrite | Trace bottom growth Nitrate reduced to nitrite |
| Broth | | | | | |

Table 4-continued

Cultural and Biochemical Characteristics of *Streptomyces platensis* Cultures

| Medium | Determination | S. platensis v. clarensis NRRL 8035 | S. platensis NRRL 2364 | S. platensis NRRL 3593 | S. platensis NRRL 3761 |
|---|---|---|---|---|---|
| Litmus milk | O | Surface pellicle Litmus reduced Partial peptonization coagulation pH 7.0 | Surface pellicle No change pH 6.8 | Surface pellicle Partial peptonization pH 7.0 | Surface pellicle Partial peptonization pH 6.8 |

S = surface
R = reverse
P = pigment
O = other characteristics

Table 5

Utilization of Carbon by *Streptomyces platensis* Cultures in the Synthetic Medium of Pridham and Gottlieb*

| | | S. platensis v. clarensis NRRL 8035 | S. platensis NRRL 2364 | S. platensis NRRL 3593 | S. platensis NRRL 3761 |
|---|---|---|---|---|---|
| | CONTROL (no carbon) compound added) | (−) | (+) | (−) | (−) |
| 1. | D-Xylose | + | + | (+) | (+) |
| 2. | L-Arabinose | (+) | (+) | (+) | (−) |
| 3. | Rhamnose | (−) | (+) | (−) | (−) |
| 4. | D-Fructose | + | + | + | + |
| 5. | D-Galactose | + | + | + | + |
| 6. | D-Glucose | o | + | + | + |
| 7. | D-Mannose | + | + | + | + |
| 8. | Maltose | + | + | + | + |
| 9. | Sucrose | + | + | + | + |
| 10. | Lactose | + | + | + | + |
| 11. | Celloboise | + | + | + | (−) |
| 12. | Raffinose | + | (+) | + | + |
| 13. | Dextrin | + | + | + | + |
| 14. | Inulin | (−) | (−) | (−) | (−) |
| 15. | Soluble starch | + | + | + | + |
| 16. | Glycerol | + | + | + | + |
| 17. | Dulcitol | (−) | (+) | (−) | (−) |
| 18. | D-Mannitol | + | + | + | + |
| 19. | D-Sorbitol | + | + | + | + |
| 20. | Inositol | + | + | + | + |
| 21. | Salicin | − | − | − | (−) |
| 22. | Phenol | − | − | − | − |
| 23. | Cresol | − | − | − | − |
| 24. | Na Formate | − | − | − | − |
| 25. | Na Oxalate | (−) | (−) | − | − |
| 26. | Na Tartrate | (−) | (−) | (−) | (−) |
| 27. | Na Salicylate | − | − | − | − |
| 28. | Na Acetate | (+) | (+) | (−) | (+) |
| 29. | Na Citrate | + | (+) | (+) | (+) |
| 30. | Na Succinate | + | (+) | (+) | (+) |

+ = Good utilization
(+) = Poor utilization
(−) = Doubtful utilization
− = No utilization
*Pridham, I.G., and D. Gottlieb. 1948. The utilization of carbon compounds by some Actino-mycetales as an aid for species determination. J. Bacteriol. 56:107–114

Table 6

Utilization of Carbon Compounds by *Streptomyces platensis* Cultures in the Synthetic Medium of Shirling and Gottlieb*

| | S. platensis v. clarensis NRRL 8035 | S. platensis NRRL 2364 | S. platensis NRRL 3593 | S. platensis NRRL 3761 |
|---|---|---|---|---|
| CONTROLS | | | | |
| Negative-basal medium | Slight growth | Slight growth | Slight growth | Slight growth |
| Positive-basal medium plus D-glucose | Good growth | Good growth | Good growth | Good growth |
| CARBON COMPOUNDS | | | | |
| L-Arabinose | ++ | ++ | ++ | + |
| Sucrose | ++ | ++ | ++ | ++ |
| D-Xylose | + | + | ± | ± |
| Inositol | ++ | ++ | ++ | ++ |
| D-Mannitol | ++ | ++ | ++ | ++ |
| D-Fructose | ++ | ++ | ++ | ++ |
| Rhamnose | ± | ± | ± | ± |
| Raffinose | ++ | ++ | ++ | ++ |

Table 6-continued
Utilization of Carbon Compounds by *Streptomyces platensis* Cultures in the Synthetic Medium of Shirling and Gottlieb*

|  | S. platensis v. clarensis NRRL 8035 | S. platensis NRRL 2364 | S. platensis NRRL 3593 | S. platensis NRRL 3761 |
|---|---|---|---|---|
| Cellulose | − | − | − | − |

++ Strong utilization
+ Positive utilization
+ Utilization doubtful
− Utilization negative

*Shirling, E. B., and D. Gottlieb. 1966. Methods for characterization of *Streptomyces* species. Int. J. Syst. Bacteriol. 16:313–340

Table 7
Antibiotics Produced by *Streptomyces platensis* Cultures

| Antibiotic | S. platensis v. clarensis NRRL 8035 | S. platensis NRRL 2364 | S. platensis NRRL 3593 | S. platensis NRRL 3761 |
|---|---|---|---|---|
| U-44,590 | + | | | |
| Oxytetracycline | | + | | |
| AH272$\alpha_2$ | | | + | |
| AH272$\beta_2$ | | | + | |
| YL-704 | | | | + |

The new compound of the invention is produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

Production of the compound of the invention can be effected at any temperature conducive to satisfactory growth of the microorganism, for example, between about 18° and 40° C., and preferably between about 20° and 32° C. Ordinarily, optimum production of the compound is obtained in about 5 to 15 days. The medium normally remains neutral during the fermentation. The final pH is dependent, in part, on the buffers present, if any and in part on the initial pH of the culture medium.

When growth is carried out in large vessels and tanks, it is preferable to use the vegetative form, rather than the spore form, of the microorganism for inoculation to avoid a pronounced lag in the production of the new compound and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the new compound, so long as a good growth of the microorganism is obtained.

A variety of procedures can be employed in the isolation and purification of the compound of the subject invention, for example, solvent extraction, partition chromatography, silica gel chromatography, liquid-liquid distribution in a Craig apparatus, absorption on resins, and crystallization from solvents.

In a preferred recovery process the compound of the subject invention is recovered from the culture medium by separation of the mycelia and undissolved solids by conventional means, such as by filtration or centrifugation. The antibiotic is recovered from the filtered or centrifuged broth by adsorption on activated carbon. The activated carbon is then washed with water to remove some impurities. This is followed by elutions with acetone: water solutions which remove the antibiotic from the activated carbon. The acetone in the eluates is removed, advantageously by evaporation, and the remaining aqueous residue is lyophilized to afford a crude preparation of antibiotic U-44,590.

A preferred purification procedure is to subject a crude preparation of U-44,590, as described above, to chromatography on silica gel from which U-44,590 is eluted. Fractions which show activity against the bacterium *Klebsiella pneumoniae* on a standard agar plate test, are pooled and taken to dryness to yield a relatively pure preparation of U-44,590. Further purification is achieved by acetylation to a crystalline diacetate derivative of U-44,590. Zemplen [G. Zemplen and E. Pacsu, Ber., 62, 1613 (1929)] de-esterification (transesterification) with sodium methoxide in methanol, and neutralization of the catalytic amount of base with carbon dioxide gives the free antibiotic U-44,590 which crystallizes readily from methanol-ethyl acetate to give a pure preparation of U-44,590.

Antibiotic U-44,590 is active against *Streptococcus hemolyticus* and, thus, can be used to disinfect instruments, utensils or surfaces when contaminated with this microorganism, where the inactivation of this microoganism is desirable. Also, U-44,590 is active against *Escherichia coil* and can be used to reduce, arrest, and/or eradicate slime production in papermill systems because of its antibacterial action against this bacterium. Anitbiotic U-44,590 can also be used to prolong the life of cultures of *Trichomonas foetus*, *Trichomonas hominis*, and *Trichomonas vaginalis* by freeing them of *Escherichia coli* contamination. Further, U-44,590 can be used to inhibit the growth of *E. coli* in hospital flower vases where it has been reported to exist and present a hazard to hospital patients. See Clinical Medicine, February, 1974, page 9.

Novel acyl derivatives of U-44,590, as disclosed herein, can be used for the same antibiotic purposes as U-44,590 in environments possessing means to deacylate the compound to U-44,590. Thus, the acyl derivatives of U-44,590 can be used to treat laboratory mice infected with Gram-negative bacteria, for example, E. coli, as disclosed herein. Further acyl derivatives of U-44,590 can be used, advantageously, to upgrade U-44,590. This is accomplished by acylating U-44,590, recovering the acylated compound relatively free of impurities, then deacylating the acylated U-44,590 to give U-44,590 in a more purified form.

The following illustrate the use in formulations of the compositions of the present invention. All percentages are by weight and all liquid solvent mixture proportions are by volume unless otherwise noted. Though the following is specific to U-44,590, it is intended that the same be applicable to derivatives of U-44,590, as disclosed herein.

The compositions of the present invention are preferably presented for administration to humans and animals in unit dosage forms, such as tablets coated and uncoated, capsules hard and soft, powders, granules, suppositories, sterile parenteral solutions or suspensions, and oral solutions or suspensions, containing suitable quantities of antibiotic U-44,590.

For oral administration either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, starch, lactose, acacia, methylcellulose, and functionally similar materials as pharmaceutical diluents or carriers. The tablets can be coated or left uncoated. Suitable coatings include a sealing coat of shellac, a carbohydrate coating (such as sugar or methylcellulose), and a lipid polish coating such as carnauba wax. Special coatings can comprise (a) lipid-type coating of a semipermeable nature for delaying absorption of the active ingredient to provide sustained action or (b) enteric substances, such as styrene-maleic acid copolymer and cellulose acetate phthalate, to resist release of the active ingredient in the stomach and permit release in the upper intestine. In their simplest embodiment, capsules, like tablets, are prepared by mixing the antibiotic with an inert pharmaceutical diluent and filling the mixture into a hard gelatin capsule of appropriate size. Soft gelatin capsules are prepared by machine encapsulation of a slurry of the antibiotic with corn oil, light liquid petrolatum or other inert oil.

Fluid unit dosage forms for oral administration such as emulsions, syrups, elixirs, and suspensions can be prepared. Emulsions can be oil-in-water or water-in-oil type and contain the active ingredient in the required amount with acceptable emulsifying agents, such as gum acacia, gum tragacanth, and the like. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent. Suspensions can be prepared of the insoluble forms in an aqueous vehicle with the aid of a suspending agent such as acacia, tragacanth, methylcellulose and the like.

Topical ointments can be prepared by dispersing the antibiotic in a suitable ointment base such as petrolatum, lanolin, polyethylene glycols, mixtures thereof, and the like. Advantageously, the antibiotic is finely divided by means of a colloid mill utilizing light liquid petrolatum as a levigating agent prior to dispersing in the ointment base. Topical creams and lotions are prepared by dispersing the antibotic in the oil phase prior to the emulsification of the oil phase in water.

For parenteral administration, fluid unit dosage forms are prepared utilizing the antibiotic and a sterile vehicle, water being preferred. The antibiotic, depending on the form and concentration used, can be either suspended or dissolved in the vehicle. In preparing solutions the water-soluble antibiotic can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompaying vial of water for injection is supplid to reconstitute the injectable solution prior to use. Parenteral suspensions are prepared in substantially the same manner except that the antibiotic is suspended in the vehicle instead of being dissolved and sterilization cannot be accomplished by filtration. The antibiotic can be sterilized by exposure to ethylene oxide before suspending in the sterile vehicle. Advantageously, a surfactant or wetting agent is included in the composition to facilitate uniform distribution of the antibiotic. For the treatment of animals by oral administration, the active ingredient is conveniently prepared in the form of a food premix. The food premix can comprise the active ingredient in admixture with an edible diluent such as starch, oatmeal, flour, calcium carbonate, talc, dried fish meal and like non-toxic, orally-acceptable diluents. The prepared premix is then added to the regular feed, thereby supplying the included medication to the animal in the course of feeding.

In addition to the administration of the compound of the Formula I as the principal active ingredient of compositions for the treatment of the conditions described herein, the said compound can be included with other types of compounds to obtain advantageous combinations of properties. Such combinations include a compound of the Formula I with antibiotics such as spectinomycin, chloramphenicol, novobiocin, dihydronovobiocin, tetracyclines (e.g., tetracycline, oxytetracycline and chlortetracycline), penicillins, erythromycin, gentamicin, kanamycin, streptomycin, neomycin, polymyxin, bacitracin, nystatin, filipin, fumagillin and endomycin to broaden the bacterial spectrum of the composition and for synergistic action against particular bacteria; analgesics such as aspirin, sodium salicylate, (acetylsalicylic acid)-anhydride, N-acetylp-aminophenol and salicylamide; antihistamines, such as chlorpheniramine maleate, diphenhydramine, promethazine, pyrathiazine, and the like; sulfas, such as sulfadiazine, sulfamethazine, sulfamerazine, sulfacetamide, sulfadimethyloxazole, sulfamethizole, and the like; antifungals such as undecylenic acid, sodium propionate, salicylanilide, sodium caprylate, and hexetidine; antivirals such as cytarabine compound or amantidine; and the vitamins.

The term unit dosage form as used in the specification and claims refers to physically discrete units suitable as unitary dosages for human subjects and animals, each unit containing a predetermined quantity of active material calculated to produce the desired therapeutic effect in association with the required pharmaceutical diluent, carrier or vehicle. The specifications for the novel unit dosage forms of this invention are dictated by and directly dependent on (a) the unique characteristics of the active material and the particular therapeutic effect to be achieved, and (b) the limitations inherent in the art of compounding such an active material for therapeutic use in humans and animals, as disclosed in detail in this specification, these being features of the present invention. Examples of suitable unit dosage forms in accord with this invention are tablets, capsules, troches, suppositories, powder packets, granules, wafers, cachets, teaspoonsful, tablespoonsful, droppersful, ampuls, vials, segregated multiples of any of the foregoing, and other forms as herein described.

The dosage of U-44,590 for treatment depends on route of administration; the age, weight, and condition of the patient; and the particular disease to be treated. For adults, a dosage schedule of from about 100 to 1,000 mg., 1 to 4 times daily (every six hours), embraces the effective range for the treatment of most conditions, For severe conditions, up to 10 Gm. or more a day can be used in divided doses. For infants the dosage is calculated on the basis of 10 mg./kg., by weight, and for children 15 to 25 mg./kg., to be administered every six hours.

The antibiotic U-44,590 is compounded with a suitable pharmaceutical carrier in unit dosage form for convenient and effective administration. In the preferred embodiments of this invention, the dosage units contain antibiotic U-44,590 in 25, 50, 100, 200, 350 and 500 mg. amounts for systemic treatment and in 0.25, 0.5, 1., 2. and 5% amounts for topical or localized treatment and in 5 to 65% w/v for parenteral preparations. The dosage of compositions containing antibiotic U44,590 and one or more other active ingredients is to be determined with reference to the usual dosage of each such ingredient. A dose of from about 2.5 mg./kg./day to about 100 mg./kg./day is preferred for systemic treatment.

The following examples are illustrative of the process and products of the present invention but are not to be construed as limiting. All percentages are by weight and solvent mixture proportions are by volume unless otherwise noted.

EXAMPLE 1

Part A. Fermentation

A soil stock of *Streptomyces platensis* var. *clarensis*. NRRL 8035, is used to inoculate a series of 500-ml. Erlenmeyer flasks, each containing 100 ml. of sterile seed medium consisting of the following ingredients:

| Glucose monohydrate | 10 Gm/l |
|---|---|
| Bacto Peptone (Difco) | 10 Gm/l |
| Bacto Yeast Extract (Difco) | 2.5 Gm/l |
| Deionized water | Balance |

The flasks are grown for 2 days at 28° C. on a Gump rotary shaker operating at 250 r.p.m.

Seed inoculum, described above, is used to inoculate a seris of 100 ml. Erlenmeyer flasks each containing 100 ml. of sterile fermentation medium. The inoculation rate is 5 ml. of seed inoculum per 100 ml. of fermentation medium. The fermentation medium consists of the following ingredients:

| Brer Rabbit Molasses (RJR Foods Inc., N.Y., N.Y. 10017) | 20 ml |
|---|---|
| Yeast Extract (Difco, Detroit, Michigan) | 1 Gm/1 |
| Glucose monohydrate | 10 Gm/1 |
| Dextrin (Corn Products Co. International Inc., International Plaza, Englewood Cliffs, New Jersey 07632) | 10 Gm/1 |
| Proteose Peptone No. 3 (Difco) | 10 Gm/1 |
| Tap water q.s. | Balance |

The presterilization pH is 7.0. The inoculated fermentation flasks are incubated at a temperature of 28 C. on a Gump rotary shaker operating at 250 r.p.m. with a 2½ inch stroke. Ucon antifoam (a synthetic defoamer supplied by Union Carbide, N.Y., N.Y.) is used if needed. Harvest is usually after 5 to 12 days of fermentation.

The antibiotic titer of the fermentation beer can be monitored by an agar plate disc assay using the bacterium *Klebsiella pneumoniae*. This bacterium is inoculated into the assay agar (Streptomycin Assay Agar, BBL, Cockeysville, Maryland 21030) of the following compositions:

| Beef extract | 1.5 Gm/liter |
|---|---|
| Yeast extract | 3.0 Gm/liter |
| Gelysate Peptone, supplied by Baltimore Biological Laboratories | 6.0 Gm/liter |
| Agar | 15.0 Gm/liter |
| Deionized H$_2$O adjust pH to 7.9 | Balance |

Sterilize at 121° C. (15 lbs. steam pressure) for 15 minutes.

Phosphate buffer (0.1N pH 6.0) is used as the diluent. The agar plates are incubated at 37° C. for 16–18 hours. Presence of antibiotic U-44,590 is evidenced by the zone of inhibition around a paper disc to which a fermentation sample was previously applied. The width of the zone of inhibition reflects the potency of the antibiotic sample. Thus, a 20 mm. zone of inhibition using a 12.7 mm. paper disc to which 0.08 ml. of antibiotic sample has been applied is expressed as one bio unit per ml. (1 BU/ml.).

Part B. Recovery

Whole fermentation beer (ca 1600 ml. assaying 5 BU/ml. against K. pneumoniae), obtained as described above, is filtered using diatomaceous earth as a filter aid. The filter cake is washed with water. The clear beer and wash (1800 ml.) is then passed through an activated carbon column. The column measures 2.8 × 44 cm. and contains 126 grams of activated carbon. The carbon column is washed with 1750 ml. water and the wash is discarded. The column is then washed with 1 liter each of a 1%, 2% and 5% acetone:water concentration. These eluates are also discarded. The column is then eluted with 1 liter each of a 10%, 25% and 50% acetone:water concentration. These eluates which contain antibiotic U-44,590, are pooled and the acetone is removed on a rotatory evaporator at 30° C./15 mm. Hg. The resulting acetone-free preparation is shell-frozen to an aqueous residue and then lyophilized; yield, 3.55 grams assaying 2 BU/mg. of U-44,590 against *K. pneumoniae*. This preparation, labeled for convenience as Solid A, is then subjected to further recovery procedures as follows.

A silica gel (Merck-Darmstadt Cat. 7734) column is prepared from 420 grams of silica gel packed in methanol:chloroform (1:1 v/v). The column measures 3.8 × 88 mm. Solid A, obtained as described above, is added on the top of the column and the column is then eluted with methanol:chloroform (1:1 v/v). Active fractions, as determined by the above-described *K. pneumoniae* assay, are pooled and the solvent is removed from said pooled fractions by use of a rotatory evaporator at 30° C./15 mm. Hg.; yield, 830 mg. assaying 7.5 BU/mg. of antibiotic U-44,590.

Part C. Purification No. 1

A preparation of antibiotic U-44,590, obtained as described above in Part B., is subjected to chromatography on silica gel using the solvent system ethyl acetate:methanol (6:1 v/v) to give a purer preparation containing U-44,590. The procedure for this purification step is as follows.

A column of silica gel (Merck-Darmstadt, 115 grams/gram of the U-44,590 preparation being chromatographed) in ethyl acetate:methanol (6:1 v/v) is prepared by pouring a slurry of silica in the solvent into the column to give a height-diameter ratio of 10:1 after being packed. The U-44,590 preparation, obtained as described above in Part B, is dissolved in methanol, silica is added (three times the weight of the U-44,590 preparation used), and this is then taken down to a dry powder on a rotatory evaporator at 40°/15 mm. Hg. The resulting dry solid is added to the top of the silica column through a small head of the solvent ethyl acetate:methanol (6:1 v/v). After a forerun of 4 liters, 50 ml. fractions are collected and assayed or activity against *K. pneumoniae*. Active fractions are also tested for solids content. Fractions greater than 50 BU/mg. are pooled and then taken to dryness in a rotatory evaporator at 40° C./7 mm. Hg. to yield a syrup Fractions and their *K. pneumoniae* (K.p.) activity and solids from a usual run are as follows:

| Fraction Number | Zone of Inhibition (using 12.7 mm. discs) | Wt. of solid in Fraction (mgm) |
|---|---|---|
| 110 | 16 | 34.5 |
| 115 | 30 | |
| 120 | 33 | 30.9 |
| 125 | 35 | |
| 130 | 37 | 40.8 |
| 135 | 37 | |
| 140 | 36 | 35.7 |
| 145 | 35 | |
| 150 | 35 | 27.0 |
| 155 | 34 | |
| 160 | 33 | 21.7 |
| 165 | 32 | |
| 170 | 31 | 21.8 |
| 175 | 30 | |
| 180 | 29 | 21.8 |
| 185 | 28 | |
| 190 | 28 | 17.9 |
| 195 | 28 | |
| 200 | 27 | 17.5 |
| 205 | 27 | |
| 210 | 26 | 14.4 |
| 215 | 26 | |
| 220 | 26 | 12.1 |
| 225 | 26 | |
| 230 | 26 | 10.0 |
| 235 | 25 | |
| 240 | 25 | 11.5 |
| 245 | 24 | |
| 250 | 24 | 11.7 |
| 255 | 23 | |
| 260 | 23 | 12.6 |
| 265 | 23 | |
| 270 | 23 | 15.4 |

Fractions 120–180, incl. are pooled and taken to dryness on a rotatory evaporator at 40°/% mm. Hg. to give a syrup wt. 2.66 g, assaying 54 K.p. BU/mg (Fractions 181–240, incl. to give a syrup, 830 mg. 32 BU/mg and fractions 241–300, incl. give a syrup, wt. 710 mg. assaying 11 BU/mg). The standard assayed 4 BU/mg. against the usual assay for this standard of 6 BU/mg.

Part D. Purification No. 2

The preparations of U-44,590, obtained as described in Part C., can be further purified to a preparation of essentially pure U-44,590 by passage over another silica gel column, using this time the solvent system methanol: methylene chloride (1:8 v/v). The procedure is as follows.

A U-44,590 preparation, as obtained in Part C., (2.28 grams) is dissolved in methanol and 7 grams of silica gel, as described in Part C., is added. The solvent from this mixture is removed on a rotary evaporator at 40° C./7 mm. Hg. The resulting solid is added to a column of silica gel [750 g., 4.8 × 96 cm, hold-up volume 1500 ml., made up in MeOH-CH$_2$Cl$_2$ (1:8 v/v)]. A forerun (1100 ml.) is collected, followed by 50 ml. fractions. Fractions 141–200, inclusive, weigh 390 mg. when taken to dryness in the form of a syrup. This material is shown to be almost pure U-44,590 by thin layer chromatography (tlc).

The tlc is conducted on silica gel plates using the solvent system MeOH-CH$_2$Cl$_2$ (1:9 v/v). Zones of the antibiotic are detected by spraying the plates with IO$_4^-$/MnO$_4^-$, and with 50% aq. H$_2$SO$_4$ followed by heating at 110° C. for ca 10 min. The Rf of the active material in this solvent system is 0.11.

Part E. Purification No. 3

The preparation of antibiotic U-44,590 obtained in Part D can be further purified by acetylation of the preparation followed by deacetylation and crystallization. The procedure for acetylation is as follows:

A sample (ca 22 g) of U-44,590 preparation, prepared as described in Part D and assaying 160 BU/mg is dissolved in pyridine (300 ml) and, to this solution stirred magnetically is added acetic anhydride (150 ml) over the course of 45 min. After standing overnight at room temperature, volatile materials are removed as completely as possible of a rotatory evaporator at 40°/15 mm. Hg., and finally under high vacuum, to give a tan syrup.

This syrup is stirred with CH$_2$Cl$_2$ (200 ml), and a colorless, flocculent precipitate is removed by filtration and washed with CH$_2$Cl$_2$ until the washings are colorless. The precipitate is discarded. The combined filtrate and washings are washed with aqueous HCl (N/20, 100 ml) twice, the aqueous layer being acidic after the second wash. The aqueous layers are discarded. The organic phase is then washed with water (100 ml), saturated aqueous NaHCO$_3$ (100 ml), again with water (100 ml), and dried ($Na_2SO_4$). The aqueous layers are discarded.

Removal of solvent on a rotatory evaporator at 40° and 15 mm. Hg. gives a dark syrup (21.10 g), which is dissolved in EtOAc (50 ml) by warming on a steambath. On cooling, crystallization occurs; the solid is removed by filtration, washed with EtOAc, and dried at 60°/15 mm. Hg., to give essentially pure 3'5'-di-O-acetylated U-44.590 (12.01 g. m.p. 123°–124.5°). Recrystallization from the same solvent gives U-44,590 diacetate, having a melting point 124–125°. This compound is then labeled U-44,474.

U-44,474 is deacetylated to afford essentially pure U-44,590 by the Zemplen procedure which is as follows.

Crystalline diacetate U-44,474 (24.90 g) is stirred magnetically in methanol (400 ml), and methanolic sodium methoxide (Stauffer Chem. Co. 25%, 5 drops) is added. Stirring is continued till the solid has dissolved (Drierite tube), and the solution allowed to stand at room temperature for about 2 hours. Solid carbon dioxide, in small pieces, is then added cautiously, with stirring, to neutralize the methoxide, and the solvent is removed on a rotatory evaporator at 40° and 15 mm. Hg., giving a colorless oil.

The residue is dissolved in methanol (50 ml) by warming on a steambath and diluted with ethyl acetate (50 ml). Crystallization occurs on cooling. The solid (12.39 g) is collected on a sintered filter at the pump, washed with methanol, and dried in a vacuum oven at 60°/15 mm. Hg. Antibiotic U-44,590 crystallizes in colorless prismatic needles, m.p. 141–142°. Removal of solvent from the filtrate plus washings on the evaporator and crystallization from methanol-ethyl acetate gives additional material (1.91 g, m.p. 140.5°–141.5°).

EXAMPLE 2

The acylation procedure described in Example 1, Part E, can be substituted by acylating U-44,590 with any readily-available acylating agent to give the acylated U-44,590 product. This acylated U-44,590 product can then be deacylated by methods well known in the art to yield a purified preparation of U-44,590. Readily-available acylating agents which can be used to acylate U-44,590, and which are within the scope of this invention, are as disclosed in U.S. Pat. No. 3,426,012, Columns 5 and 6.

EXAMPLE 3

As disclosed in Example 2, various acylates of U-44,590 can be made, and these acylates are useful to upgrade U-44,590. By following the procedure of Example 1, Part E, the 3',5'-di-esters of U-44,590 are formed. The 5'-monoesters can be formed by the use of a minimum amount of acylaing agent. The 3'-monoesters and phosphate can be formed by tritylating U-44,590 to give the 5'-trityl derivative, acylating or phosphorylating this compound with the desired acylating or phosphorylating agent, selected from those disclosed above, to give the 3'-mono-ester 5'-trityl derivative, which then can be converted to the 3'-monoester by removal of the trityl group. The tritylation procedure disclosed in U.S. Pat. No. 3,426,012, Column 4 and 5, or other standard tritylation procedures can be employed. The trityl group can be removed by using the procedure disclosed in U.S. Pat. No. 3,426,012, Column 6.

EXAMPLE 4

The 5'-phosphate of U-44,590 can be prepared by procedures as disclosed in the work of D. Mitsunobu, K. Kato, and J. Kimura [J. Amer. Chem. Soc., 91,6510 (1969)]. This compound can be used for the same purposes as U-44,590.

The compounds, described above, being the derivatives of U-44,590 which are within the scope of the subject invention, can be shown by the following structural formula

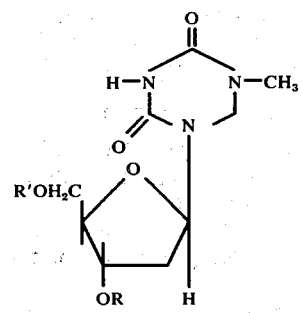

wherein R and R' are selected from the group consisting of a carboxylic acid acyl radical of from 2 to 18 carbon atoms, inclusive; or a halo-, nitro-, hydroxy-, amino-, cyano-, thiocyano-, and lower alkoxy-substituted hydrocarbon carboxylic acid acyl radical of from 2 to 18 carbon atoms, inclusive; or R is hydrogen and R' is as defined above or phosphate; or R' is hydrogen and R is a carboxylic acid acyl radical of from 2 to 18 carbon atoms, inclusive; or a halo-, nitro-, hydroxy-, amino-, cyano-, thiocyano-, and lower alkoxy-substituted hydrocarbon carboxylic acid acyl radical of from 2 to 18 carbon atoms, inclusive, or phosphate.

EXAMPLE 5 CAPSULES

One thousand two-piece hard gelatin capsules for oral use, each containing 250 mg. of antibiotic U-44,590 are prepared from the following types and amounts of materials:

| | |
|---|---|
| Antibiotic U-44,590 | 250 Gm. |
| Corn starch | 50 Gm. |
| Talc | 25 Gm. |
| Magnesium stearate | 2 Gm. |

The materials are thoroughly mixed and then encapsulated in the usual manner.

The foregoing capsules are useful for the systemic treatment of infection in adult humans by the oral administration of 1 capsule every 4 hours.

Using the procedure above, capsules are similarly prepared containing the antibiotic in 50, 100, and 350 mg. amounts by substituting 50, 100 and 350 Gm. of antibiotic for the 250 Gm. used above.

EXAMPLE 6 TABLETS

One thousand tablets for oral uses, each containing 500 mg. of antibiotic U-44,590 are prepared from the following types and amounts of materials:

| | |
|---|---|
| Antibiotic U-44,590 | 500 Gm. |
| Lactose | 125 Gm. |
| Corn starch | 65 Gm. |
| Magnesium stearate | 5 Gm. |

-continued

| | |
|---|---|
| Light liquid petrolatum | 3 Gm. |

The ingredients are thoroughly mixed and slugged. The slugs are broken down by forcing through a number sixteen screen. The resulting granules are then compressed into tablets, each tablet containing 500 mg. of antibiotic.

The foregoing tablets are useful for systemic treatment of infections in adult humans by oral administration of 1 tablet every 4 hours. In severe conditions, 2 to 4 tablets can be administered every 4 hours.

Using the above procedure, except for reducing the amount of antibiotic to 200 Gm., tablets containing 200 mg. of antibiotic are prepared.

EXAMPLE 7 TABLETS

One thousand oral tablets, each containing 125 mg. of antibiotic U-44,590 and a total of 250 mg. (83.3 mg. each) of sulfadiazine, sulfamerazine, and sulfamethazine, are prepared from the following types and amounts of materials:

| | |
|---|---|
| Antibiotic U-44,590 | 125 Gm. |
| Sulfadiazine | 83.3 Gm. |
| Sulfamerazine | 83.3 Gm. |
| Sulfamethazine | 83.3 Gm. |
| Lactose | 50 Gm. |
| Corn starch | 50 Gm. |
| Calcium stearate | 25 Gm. |
| Light liquid petrolatum | 5 Gm. |

The ingredients are thoroughly mixed and slugged. The slugs are broken down by forcing through a number sixteen screen. The resulting granules are then compressed into tablets, each tablet containing 125 mg. of antibiotic and a total of 250 mg. (83.3 mg. each) of sulfadiazine, sulfamerazine, and sulfamethazine.

The foregoing tablets are useful for a systemic treatment of infections by the oral administration of 4 tablets first and then 1 every 6 hours.

For treatment of urinary infections, the triple sulfas in the above formulation is advantageously replaced by 250 Gm. of sulfamethylthiadiazole or 250 Gm. of sulfacetamide.

EXAMPLE 8 GRANULES

2367 Gm. of a granulation suitable for reconstitution with water prior to use is prepared from the following types and amounts of ingredients:

| | |
|---|---|
| Antibiotic U-44,590 | 150 Gm. |
| Sucrose, powdered | 2155 Gm. |
| Flavor | 60 Gm. |
| Sodium metabisulfite | 2 Gm. |

The antibiotic U-44,590, sugar, flavor, and sodium metabisulfite are mixed together until thoroughly blended. The powder mixture is wetted with water and forced through a screen to form granules. The granules are dried and 23.67 Gm. filled into 60 ml. bottles. Prior to use, sufficient water is added to the granules to make 60 ml. of composition.

The foregoing composition is useful for systemic treatment of infection, particularly in children at a dose of one teaspoonful (5 ml.) 4 times daily.

EXAMPLE 9 ORAL SYRUP 1000 ml. of an aqueous preparation for oral use, containing in each 5 ml. dose, 250 mg. of antibiotic U-44,590 is prepared from the following types and amounts of ingredients:

| | |
|---|---|
| Antibiotic U-44,590 | 50 Gm. |
| Citric acid | 2 Gm. |
| Benzoic acid | 1 Gm. |
| Sucrose | 700 Gm. |
| Tragacanth | 5 Gm. |
| Lemon oil | 2 Gm. |
| Deionized water q.s. | 1000 ml. |

The citric acid, benzoic acid, sucrose, tragacanth, and lemon oil are dispersed in sufficient water to make 850 ml. of solution. The antibiotic is stirred into the syrup until uniformly distributed. Sufficient water is added to make 1000 ml.

The composition so prepared is useful in the systemic treatment of infection due to *Klebsiella pneumoniae* in adult humans at a dose of 1 or 2 teaspoons 4 times a day. In severe conditions, 1 or 2 tablespoons (15 to 30 ml.) can be administered 4 times a day.

EXAMPLE 10 PARENTERAL SUSPENSION

A sterile aqueous suspension for intramuscular use, containing in 1 ml. 200 mg. of antibiotic U-44,590 is prepared from the following types and amounts of materials:

| | |
|---|---|
| Antibiotic U-44,590 | 200 Gm. |
| Lidocaine hydrochloride | 5 Gm. |
| Methylparaben | 2.5 Gm. |
| Propylparaben | 0.17 Gm. |
| Water for injection q.s. | 1000 ml. |

All of the ingredients, except the antibiotic, are dissolved in the water and the solution sterilized by filtration. To the sterile solution is added the sterilized antibiotic and the final suspension is filled into sterile vials and the vials sealed.

EXAMPLE 11 PARENTERAL SOLUTION

A sterile aqueous solution for intramuscular use, containing in 1 ml., 150 mg. of antibiotic U-44,590, is prepared from the following types and amounts of ingredients:

| | |
|---|---|
| Antibiotic U-44,590 | 150 Gm. |
| Lactose | 50 Gm. |
| Water for injection q.s. | 1000 ml. |

The antibiotic and lactose are dissolved in the water and the solution sterilized by filtration. The sterile solution in the amount of 2 ml., is aseptically filled into sterile vials and frozen. The water is removed under high vacuum and the vials containing the lyophilized powder are sealed. Just prior to use, sufficient water for injection to make 2 ml. of solution is added to the vial.

EXAMPLE 12 TOPICAL OINTMENT

1000 Gm. of 2% ointment is prepared from the following types and amounts of ingredients:

| | |
|---|---|
| Antibiotic U-44,590 | 20 Gm. |
| Zinc oxide | 50 Gm. |
| Calamine | 50 Gm. |
| Liquid petrolatum (heavy) | 250 Gm. |
| Wool fat | 200 Gm. |
| White petrolatum q.s. | 1000 Gm. |

The white petrolatum and wool fat are melted and 100 Gm. of liquid petrolatum added thereto. The antibiotic, zinc oxide and calamine are added to the remaining liquid petrolatum and the mixture milled until the powders are finely divided and uniformly dispersed. The powder mixture is stirred into the white petrolatum mixture and stirring continued until the ointment congeals.

The foregoing ointment is usefully applied topically to the skin of mammals for the treatment of infection.

The foregoing composition can be prepared by omitting the zinc oxide and calamine.

Following the procedure above, ointments are similarly prepared containing antibiotic U-44,590 in 0.25, 0.5, 1.0, and 5% amounts of substituting 2.5, 5, 10, and 50 Gm. of antibiotic for the 20 Gm. used above.

EXAMPLE 13 TROCHES 10,000 troches are prepared from the following types and amounts of ingredients:

| | |
|---|---|
| Antibiotic U-44,590 | 100 Gm. |
| Neomycin sulfate | 50 Gm. |
| Ethyl aminobenzoate | 50 Gm. |
| Polymyxin B sulfate (10,000 units/mg.) | 1 Gm. |
| Calcium stearate | 150 Gm. |
| Powdered Sucrose q.s. | 5000 Gm. |

The powdered materials are mixed thoroughly and then compressed into half gram troches following the usual techniques for the preparation of compressed tablets.

The troches are held in the mouth and allowed to dissolve slowly to provide treatment for the mouth and throat of humans.

EXAMPLE 14 SUPPOSITORY

One thousand suppositories, each weighing 2.5 Gm. and containing 100 mg. of antibiotic U-44,590 are prepared from the following types and amounts of ingredients:

| | |
|---|---|
| Antibiotic U-44,590 | 100 Gm. |
| Polymyxin B sulfate (10,000 units/mg.) | 1.25 Gm. |
| Ethyl aminobenzoate | 75 Gm. |
| Zinc oxide | 62.5 Gm. |
| Propylene glycol | 162.5 Gm. |
| Polyethylene glycol 4000 q.s. | 2500 Gm. |

The antibiotic U-44,590, polymixin B sulfate, ethyl aminobenzoate, and zinc oxide are added to the propylene glycol and the mixture milled until the powders are finely divided and uniformly dispersed. The polyethylene glycol 4000 is melted and the propylene glycol dispersion added slowly with stirring. The suspension is poured into molds at 40° C. The composition is allowed to cool and solidify and then removed from the mold and each suppository foil wrapped.

The foregoing suppositories are inserted rectally or vaginally for local treatment of inflammation and infection.

EXAMPLE 15 MASTITIS OINTMENT

1000 Gm. of an ointment for the treatment of mastitis in dairy cattle is prepared from the following types and amounts of ingredients:

| | |
|---|---|
| Antibiotic U-44,590 | 50 Gm. |
| Prednisolone acetate | 0.5 Gm. |
| Light liquid petrolatum | 300 Gm. |
| Chlorobutanol, anhydrous | 5 Gm. |
| Polysorbate 80 | 5 Gm. |
| 2% Aluminum monostearate - peanut oil gel | 400 Gm. |
| White petrolatum q.s. | 1000 Gm. |

The antibiotic and prednisolone acetate are milled with the light liquid petrolatum until finely divided and uniformly dispersed. The chlorobutanol, polysorbate 80, peanut oil gel and white petrolatum are heated to 120° F. to form a melt and the liquid petrolatum dispersion stirred in. With continued stirring the dispersion is allowed to cool (and congeal) to room temperature and is filled into disposable mastitis syringes in 10 Gm. doses.

EXAMPLE 16 ANIMAL FEED

1000 Gm. of a feed mix is prepared from the following types and amounts of ingredients:

| | |
|---|---|
| Antibiotic U-44,590 | 10 Gm. |
| Soybean meal | 400 Gm. |
| Fish meal | 400 Gm. |
| Wheat germ oil | 50 Gm. |
| Sorghum molasses | 140 Gm. |

The ingredients are mixed together and pressed into pellets.

The composition can be fed to laboratory animals, i.e., rats, mice, guinea pigs, and rabbits for prophylaxis during shipping.

For larger animals the composition can be added to the animal's regular feed in an amount calculated to give the desired dose of antibiotic.

EXAMPLE 17

Following the procedure of each of the preceding Examples 5 through 16, the diacetyl derivative of U-44,590 as well as the other derivatives of U-44,590, as disclosed herein, can be substituted in an equivalent amount of antibiotic U-44,590 shown in the examples to provide similar therapeutic properties.

Additional characterization of U-44,474, prepared as described in Example 1, Part E, is as follows:

Elemental Analysis: Calcd. for $C_{13}H_{13}N_3O_7$ Found: C, 47.41; H, 5.82; N, 12.76; O, 34.01.

Molecular Weight: 329 (Determined by mass spectrometry)

Infrared Absorption Spectra: U-44,474 has a characteristic infrared absorption spectrum when suspended in a mineral oil mull. Peaks are observed at the following wave lengths expressed in reciprocal centimeters:

| Band Frequency (Wave Numbers) | Intensity |
|---|---|
| 3210 | M |
| 3080 | M |
| 2960 (oil) | S |
| 2930 (oil) | S |
| 2860 (oil) | S |
| 1750 | S |
| 1732 | S |
| 1702 | S |
| 1520 | S |
| 1468 (oil) | S |
| 1411 | M |
| 1379 (oil) | S |
| 1358 | W |
| 1327 | W |
| 1318 | W |
| 1310 | W |
| 1298 | W |
| 1280 | M |
| 1250 | S |
| 1227 | S |
| 1188 | M |
| 1148 | W |
| 1113 | W |
| 1097 | S |
| 1057 | M |
| 1030 | S |
| 1011 | M |
| 1000 | M |
| 987 | M |
| 964 | M |
| 957 | M |
| 950 | M |
| 936 | W |
| 892 | M |
| 863 | M |
| 828 | M |
| 791 | M |
| 775 | M |
| 755 | M |
| 740 | W |
| 721 (oil) | W |
| 675 | W |
| 668 | W |

U-44.474 also has a characteristic infrared absorption spectrum when pressed in a KBr disc. Peaks are observed at the following wave lengths expressed in reciprocal centimeters:

| Band Frequency (Wave Numbers) | Intensity |
|---|---|
| 3420 (water) | W |
| 3210 | M |
| 3080 | M |
| 2970 | W |
| 2960 | W |
| 2930 | W |
| 2880 | W |
| 2830 | W |
| 1750 | S |
| 1732 | S |
| 1703 | S |
| 1517 | M |
| 1468 | S |
| 1410 | M |
| 1382 | M |
| 1370 | M |
| 1248 | S |
| 1227 | S |
| 1186 | M |
| 1145 | W |
| 1095 | M |
| 1055 | M |
| 1030 | M |
| 1011 | M |
| 999 | M |
| 986 | M |
| 963 | M |
| 949 | M |
| 932 | W |
| 890 | M |
| 863 | M |
| 825 | M |
| 790 | M |
| 773 | M |
| 754 | M |
| 739 | W |
| 668 | W |

We claim:
1. A therapeutic composition comprising, in unit dosage form, from about 25 to about 500 mg. of a compound of the formula

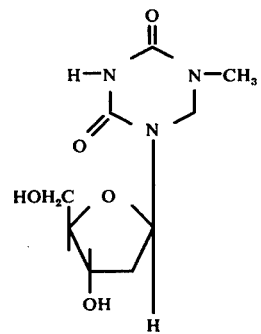

in combination with a pharmaceutical carrier.

2. A therapeutic composition, according to claim 1, comprising from about 5% to about 80% of the compound of the formula.

3. A sterile composition for parenteral administration comprising from about 5% to about 65%, w/v, of a compound of the formula

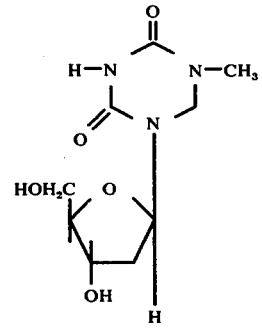

in combination with a sterile vehicle.

4. The process for treating susceptible microbial infectious disease in humans and animals which comprises the administering to the bacterial host a therapeutic amount of a compound of the formula

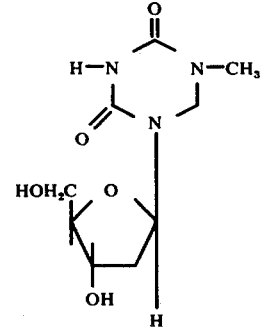

in combination with a pharmaceutical carrier.

5. A process, according to claim 4, wherein the compound of the formula is administered in unit dosage form in an amount of from about 25 to about 500 mg. of said compound in association with a pharmaceutical carrier.

6. A process, according to claim 4, wherein the compound of the formula is administered to the infected host in unit dosage form in an amount of from about 2.5 mg./kg./day to about 100 mg./kg./day of said compound in association with a pharmaceutical carrier.

7. A process of prophylactic treatment for the prevention of susceptible microbial infectious disease comprising the administration to a disease-susceptible host of an effective amount of a compound of the formula

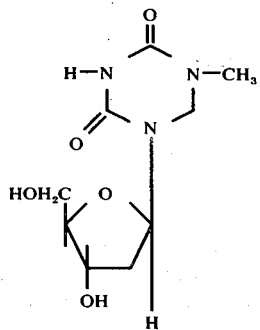

in combination with a phamaceutical carrier.

8. A process, according to claim 7, wherein the compound of the formula is administered in unit dosage form in an amount of from about 25 to about 500 mg. of said compound in association with a pharmaceutical carrier.

9. A process for treating susceptible Herpes viral infectious disease in humans and animals which comprises the administering to the viral host a therapeutic amount of a compound of the formula

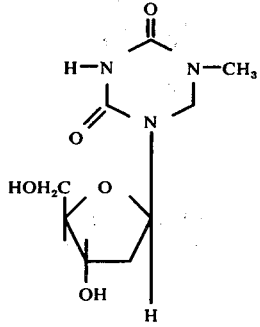

in combination with a pharmaceutical carrier.

10. A process, according to claim 9, wherein the compound of the formula is administered in unit dosage form in an amount of from about 25 to about 500 mg. of said compound in association with a pharmaceutical carrier.

11. A process, according to claim 9, wherein the compound of the formula is administered to the infected host in unit dosage form in an amount of from about 2.5 mg./kg.day to about 100 mg. kg. day of said compound in association with a pharmaceutical carrier.

12. A process of prophylactic treatment for the prevention of susceptible Herpes viral infectious disease comprising the administering to a viral disease-susceptible host of an effective amount of a compound of the formula

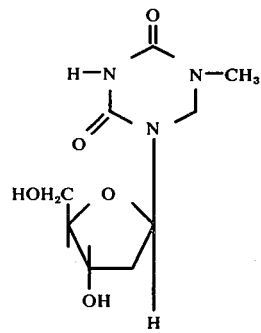

in combination with a pharmaceutical carrier.

13. A process, according to claim 12, wherein the compound of the formula is administered in unit dosage form in an amount of from about 25 to about 500 mg. of said compound in association with a pharmaceutical carrier.

14. A therapeutic composition comprising, in unit dosage form, from about 25 to about 500 mg. of a member selected from the group consisting of a compound of the formula

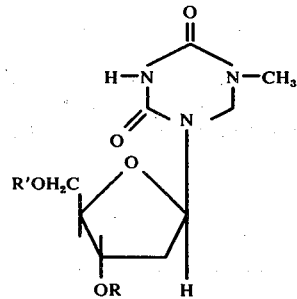

wherein R and R' are selected from the group consisting of a carboxylic acid acyl radical of from 2 to 18 carbon atoms, inclusive; or a halo-, nitro-, hydroxy-, amino-, cyano-, thiocyano-, and lower alkoxy-substituted hydrocarbon carboxylic acid acyl radical of from 2 to 18 carbon atoms, inclusive; R is hydrogen and R' is as defined above or phosphate; or R' is hydrogen and R is a carboxylic acid acyl radical of from 2 to 18 carbon atoms, inclusive; or a halo-, nitro-, hydroxy-, amino-, cyano-, thiocyano-, and lower alkoxy-substituted hydrocarbon carboxylic acid acyl radical of from 2 to 18 carbon atoms, inclusive, or phosphate, in combination with a pharmaceutical carrier.

15. A therapeutic composition, according to claim 14, comprising from about 5% to about 80% of the compound of the formula.

16. A sterile composition for parenteral administration comprising from about 5% to about 65% w/v, of a member selected from the group consisting of a compound of the formula

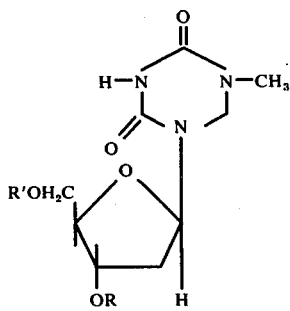

wherein R and R' are as defined in claim 14, in combination with a sterile vehicle.

17. The process for treating susceptible microbial infectious disease in humans and animals which comprises the administering to the bacterial host a therapeutic amount of a compound of the formula

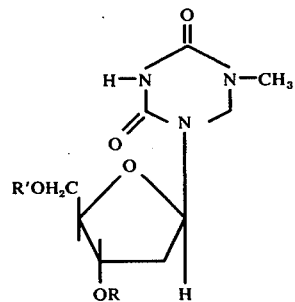

wherein R and R' are as defined in claim 14, in combination with a pharmaceutical carrier.

18. A process, according to claim 17, wherein the compound of the formula is administered in unit dosage form in an amount of from about 25 to about 500 mg. of said compound in association with a pharmaceutical carrier.

19. A process, according to claim 17, wherein the compound of the formula is administered to the infected host in unit dosage form in an amount of from about 2.5 mg./kg./day to about 100 mg./kg./day of said compound in association with a pharmaceutical carrier.

20. A process of prophylactic treatment for the prevention of susceptible microbial infectious disease comprising the administering to a disease-susceptible host an effective amount of a compound of the formula

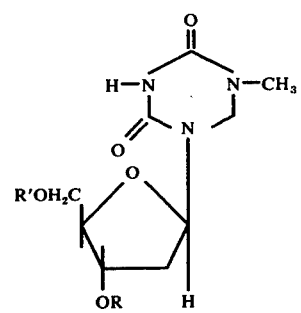

wherein R and R' are as defined in claim 14, in combination with a pharmaceutical carrier.

21. A process, according to claim 20, wherein the compound of the formula is administered in unit dosage form in an amount of from about 25 to about 500 mg. of said compound in association with a pharmaceutical carrier.

22. A process for treating susceptible Herpes viral infectious disease in humans and animals which comprises the administering to the viral host a therapeutic amount of a compound of the formula

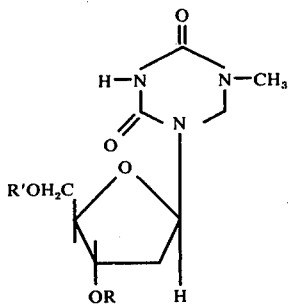

wherein R and R' are as defined in claim 14, in combination with a pharmaceutical carrier.

23. A process, according to claim 22, wherein the compound of the formula is administered in unit dosage form in an amount of from about 25 to about 500 mg. of said compound in association with a pharmaceutical carrier.

24. A process, according to claim 22, wherein the compound of the formula is administered to the infected host in unit dosage form in an amount of from about 2.5 mg./kg./day to about 100 mg./kg./day of said compound in association with a pharmaceutical carrier.

25. A process of prophylactic treatment for the prevention of susceptible Herpes viral infectious disease comprising the administering to a viral disease-susceptible host an effective amount of a compound of the formula wherein R and R' are as defined in claim 14, in combination with a pharmaceutical carrier.

26. A process, according to claim 25, wherein the compound of the formula is administered in unit dosage form in an amount of from about 25 to about 500 mg. of said compound in association with a pharmaceutical carrier.

27. A therapeutic composition, according to claim 14, wherein the compound is U-44,474, which is characterizable by the formula

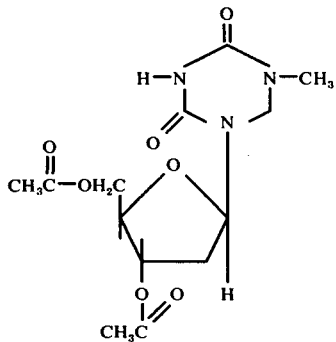

28. A sterile composition for parenteral administration, according to claim 16, wherein the compound is U-44,474, which is characterizable by the formula

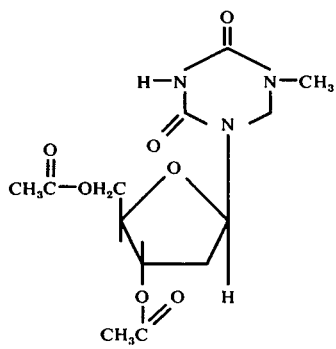

29. A process for treating susceptible microbial infectious disease in humans and animals, according to claim 17, wherein the compound administered to the bacterial host is U-44,474, which is characterizable by the formula

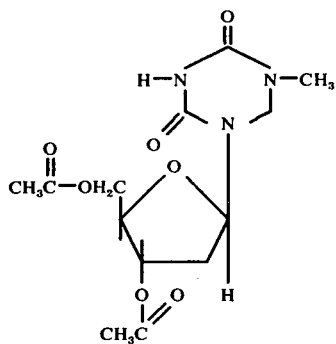

30. A process of prophylactic treatment for the prevention of susceptible microbial infectious disease, according to claim 20, wherein the compound administered to a disease-susceptible host is U-44,474, which is characterizable by the formula

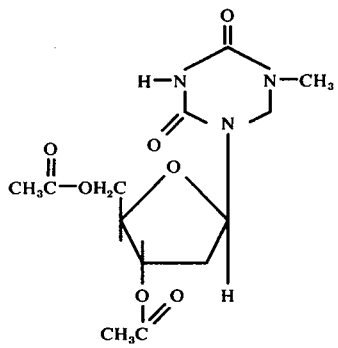

31. A process for treating susceptible Herpes viral infectious disease in humans and animals, according to claim 22, wherein the compound administered to the viral host is U-44,474, which is characterizable by the formula

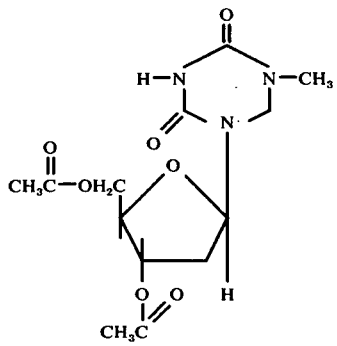

32. A process of prophylactic treatment for the prevention of susceptible Herpes viral infectious disease, according to claim 25, wherein the compound administered to a viral disease-susceptible host is U-44,474, which is characterizable by the formula

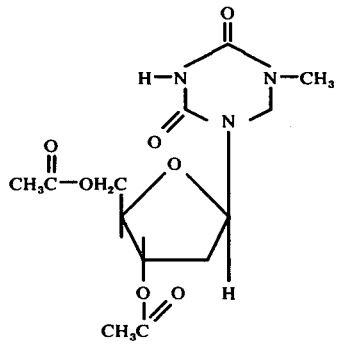

* * * * *

UNITED STATES PATENT OFFICE
CERTIFICATE OF CORRECTION

Patent No. 4,022,889  Dated May 10, 1977

Inventor(s) Brian Bannister, et al.

It is certified that error appears in the above-identified patent and that said Letters Patent are hereby corrected as shown below:

Column 1, line 29: "is" should read -- its --.
Column 1, line 39: "$H_2O$]" should read -- $H_2O$) --.
Column 1, line 44: "Spectra;" should read -- Spectra: --.
Column 3, line 21: "$\alpha$" should read -- $\beta$ --.
Column 3, line 27: "µg/ml" should read -- (µg/ml) --.
Column 3, line 47: "anerobically)" should read -- anaerobically) --.
Columns 7-8, Table 2, 3rd. Column, first line: "2lh(g) to d(g)" should read -- 2ih(g) to d(g) --.
Columns 7-8, Table 2, 3rd. Column, tenth line: "3ll(m) to 3fe(m)" should read -- 3li(m) to 3fe(m) --.
Column 9, Table 3, 2nd. Column, Ninth line: "antigue" should read -- antique --.
Column 11-12, Table 4, 1st. Column, Tenth line: "asparagin" should read -- asparagine --.
Columns 11-12, Table 4, 4th. Column, line 49: "Cream-yellow-" should read -- Cream-yellow-pink --.
Columns 11-12, Table 4, 4th. Column, line 67: "liquifaction" should read -- liquefaction --.
Columns 13-14, Table 5, 2nd. Column, lines 2-3: "(no carbon) compound added)" should read -- (no carbon compound added) --.
Columns 13-14, Table 5, 3rd. Column, #6 of the table: "o" should read -- + --
Columns 13-14, Table 5, 2nd. Column, #11 of the table: "Celloboise" should read -- Cellobiose --.
Columns 13-14, Table 5, 5th line after the table: "*Pridham, i.G.," should read -- *Pridham, T. G., --.
Column 15, Table 6, 3rd. line after table: "+ Utilization doubtful" should read -- ± Utilization doubtful --.
Column 16, line 60: "coil" should read -- coli --.
Column 19, line 67: "100 ml." should read -- 500 ml. --.
Column 22, line 13: "40°/% mm." should read -- 40°/7 mm. --.
Column 23, line 9: "U-44.590" should read -- U-44,590 --.

UNITED STATES PATENT OFFICE
CERTIFICATE OF CORRECTION

Patent No. 4,022,889  Dated May 10, 1977

Inventor(s) Brian Bannister, et al.

It is certified that error appears in the above-identified patent and that said Letters Patent are hereby corrected as shown below:

Column 28, line 60: "$C_{13}H_{13}N_3O_7$" should read -- $C_{13}H_{19}N_3O_7$ --.
Column 29, line 36: "U-44.474" should read -- U-44,474 --.
Column 31, line 66, Claim 11: "mg./kg.day" should read -- mg./kg./day --.

Signed and Sealed this

Fifteenth Day of September 1981

[SEAL]

Attest:

GERALD J. MOSSINGHOFF

Attesting Officer  Commissioner of Patents and Trademarks